United States Patent
Zhang (Ken) et al.

(10) Patent No.: US 6,863,861 B1
(45) Date of Patent: Mar. 8, 2005

(54) PROCESS FOR FORMING A MEDICAL DEVICE BALLOON

(75) Inventors: Xiao Kang Zhang (Ken), Champlin, MN (US); Daniel Horn, Shoreview, MN (US); Nao Pao Lee, Brooklyn Park, MN (US); Victor Leo Schoenle, Greenfield, MN (US)

(73) Assignee: Boston Scientific SciMed, Inc., Maple Grove, MN (US)

( * ) Notice: Subject to any disclaimer, the term of this patent is extended or adjusted under 35 U.S.C. 154(b) by 314 days.

(21) Appl. No.: 09/672,330

(22) Filed: Sep. 28, 2000

(51) Int. Cl.[7] .............................................. B29C 47/00
(52) U.S. Cl. .................... 264/530; 264/516; 264/209.1; 264/209.3
(58) Field of Search ............................. 264/530, 209.3, 264/209.1, 516

(56) References Cited

U.S. PATENT DOCUMENTS

| | | | |
|---|---|---|---|
| 4,490,421 A | 12/1984 | Levy | 428/35 |
| 5,017,325 A | 5/1991 | Jackowski et al. | 264/521 |
| 5,087,394 A | 2/1992 | Keith | 204/22 |
| 5,223,205 A | 6/1993 | Jackowski et al. | 264/521 |
| 5,270,086 A * | 12/1993 | Hamlin | 428/35.2 |
| 5,348,538 A | 9/1994 | Wang et al. | 604/96 |
| 5,556,383 A | 9/1996 | Wang et al. | 604/96 |
| 5,587,125 A | 12/1996 | Roychowdhury | 264/515 |
| 5,749,851 A | 5/1998 | Wang | 604/96 |
| 5,807,520 A | 9/1998 | Wang et al. | 264/520 |
| 2003/0030189 A1 * | 2/2003 | Wang et al. | 264/532 |
| 2003/0167067 A1 * | 9/2003 | Wang et al. | 606/192 |

FOREIGN PATENT DOCUMENTS

| | | |
|---|---|---|
| EP | 274 411 A2 | 1/1988 |
| EP | 592 885 A2 | 9/1993 |
| WO | 97/17098 | 5/1997 |
| WO | 97/32624 | 9/1997 |
| WO | 99/44649 | 9/1999 |
| WO | 00/002613 | 1/2000 |

* cited by examiner

*Primary Examiner*—Michael P. Colaianni
*Assistant Examiner*—Monica A. Fontaine
(74) *Attorney, Agent, or Firm*—Vidas, Arrett & Steinkraus

(57) ABSTRACT

A balloon blowing process which involves radial expansion of an extruded tubing segment which has been subjected to a stretching step prior to radial expansion, the process utilizing an internal pressure and a temperature which together cause at least a portion of the tubing to expand to an interior diameter (ID) which is greater than the interior diameter of the extruded segment prior to extrusion.

12 Claims, 2 Drawing Sheets

PROCESS FOR FORMING A MEDICAL DEVICE BALLOON

BACKGROUND OF THE INVENTION

Devices having a balloon mounted at the distal end of a catheter are useful in a variety of medical procedures. A balloon reservoir may be used to deliver a biologically compatible fluid, such a radiologically opaque fluid for contrast x-rays, to a site within the body. Radial expansion of a balloon may be used to expand or inflate a stent positioned within the body. A balloon may also be used to widen a vessel into which the catheter is inserted by dilating the blocked vessel. For example, in the technique of balloon angioplasty, a catheter is inserted for long distances into blood vessels of extremely reduced diameter and used to release or dilate stenoses therein by balloon inflation. These applications require extremely thin walled high strength relatively inelastic balloons of accurately predictable inflation properties.

Dilatation balloons made from PET (polyethylene terephthalate) are well known and widely used for angioplasty, stent placement, treatments in the gastrointestinal, urethral, or reproductive tracts, and for other medical purposes. Other polymer materials have also been reported to be useful in such applications and some of those polymer materials have also been used commercially, for instance, polyethylene, polyvinyl chloride, Surlyn® polyethylene ionomer copolymer, nylon 12, Pebax® polyamide-polyether-polyester block copolymer, and polyester-polyether block copolymers.

Polymer balloons for medical devices are conventionally made by radially expanding a tubular parison of a polymer material at a temperature above the glass transition temperature (Tg) of the material. (In the present application "the glass transition temperature" when referring to a material which has more than one glass transition refers to the highest glass transition temperature displayed by the material). Sometimes the tubular parison is simply an extruded tube. However, frequently the extruded tube is axially stretched prior to being radially expanded. Axial stretching may be undertaken at ambient or at a temperature above ambient temperature. See U.S. Pat. No. 4,490,421 to Levy.

In U.S. Pat. No. 5,017,325 and U.S. Pat. No. 5,223,205, a process and apparatus are described for making balloons of polyamide polymer. In the process an extruded tubing segment is subjected to an initial stretching step, an initial blowing step, and then to at least one further stretching step and at least one further blowing step.

In WO 99/44649, corresponding to U.S. Pat. No. 6,465,067, both of which are incorporated here by reference, there is described a process for blowing balloons of a material having a high crystallization rate from an extruded tubing segment. The process involves stretching the tubing in a manner which produces a propagating necking of at least a portion of the tubing segment while simultaneously subjecting the tubing to an internal pressure above ambient and then radially expanding the necked portion of the tubing at a temperature above the Tg of the material. It has been observed that in the practice of this process, the necking step reduces both the exterior diameter and the interior diameter of the tubing segment.

SUMMARY OF THE INVENTION

The present invention in one aspect is a balloon blowing process which involves radial expansion of an extruded tubing segment which has been subjected to a stretching step prior to radial expansion, the process utilizing an internal pressure and a temperature which together cause at least a portion of the tubing to expand to an interior diameter (ID) which is greater than the interior diameter of the tubing segment as extruded. In particular the invention is a process for producing a balloon comprising:

(a) axially stretching an extruded tubing segment made of a polymer material while pressurizing the tubing at an internal pressure above ambient pressure, to produce a stretched parison, the extruded tubing segment having a first ID and the polymer material having a glass transition temperature above ambient temperature, and then (b) blowing the balloon by expanding the stretched parison in a mold at a temperature above said glass transition temperature, wherein said axially stretching comprises the step (a)(i) of subjecting the tubing to a temperature and internal pressure which is sufficient to expand the ID of at least a portion of the stretched parison to a second ID greater than the first ID.

DETAILED DESCRIPTION OF THE INVENTION

Figure 1:
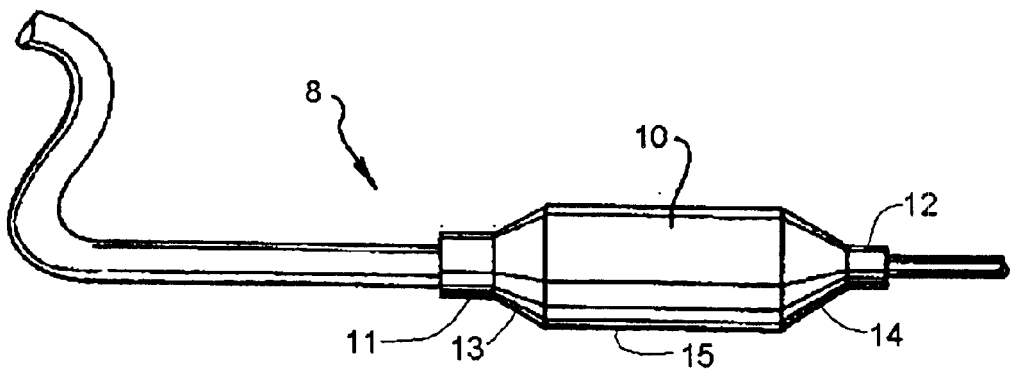
FIG. 1 is a fragmentary side view of a medical catheter having mounted thereon a balloon produced in accordance with the invention.

Referring to FIG. 1 there is shown therein a medical device catheter 8 having mounted thereon a balloon 10, suitable for mounting on a catheter. Balloon 10 comprises oppositely disposed waist portions 11, 12, cone portions 13, 14, and body portion 15. Balloon 10 is made from polymer material.

Polymers

The polymer materials which may be used in the invention may be essentially any polymer material which is suitable for forming catheter balloon. Many such polymers are known, including olefin/ionomer copolymers such as sold under the mark Surlyn®; various polyesters, including polyethylene terephthalate (PET), polybutylene terephthalate (PBT), polyethylene naphthalate (PEN), and ethylene terephthalate, butylene terephthalate and ethylene naphthalate copolymers; polyamides, including aliphatic polyamides, such as nylon 11 and nylon 12, and aromatic polyamides; certain polyurethanes, especially polyurethanes derived from polyester polyols and/or aromatic polyisocyanates; polyetheretherketone (PEEK); and block copolymers such as segmented PBT-polybutylene oxide block copolymers sold under the Hytrel® and Arnitel® trademarks and the segmented polyamide-polyether-polyesters sold under the Pebax® trademark; polycarbonates; poly(meth)acrylates and maleate polymers. Preferred polymer materials include polyamide/polyether/polyester, polyamide/polyether, and polyester/polyether block copolymers; ethylene terephthalate polymers and copolymers; butylene terephthalate polymers and copolymers; ethylene naphthalate polymers and copolymers; and polyamides Polymer blends may also be used in some cases, typically comprising at least one member of the blend being a polymer from the group described above.

Process

Catheter balloons, such as depicted in FIG. 1, may be formed from tubular extrusions of the polymer material. Tubular extrusions may be prepared according to conventional procedures and segmented to form tubular parisons from which the medical device balloons will be formed. An extrusion of this type is depicted as 20 in FIG. 2.

The parisons may be formed of a single layer of polymer material or of multiple layers of the same or different polymers. Multilayer parisons may be formed by coextrusion or by other techniques known in the art.

For medical catheter balloons suited for dilatation or stent placement applications with nominal diameters of about 1.5–24 mm, extruded wall thicknesses (single wall basis) in the range of 0.003–0.036 inch (0.076–0.91 mm) and outer diameters in the range of 0.015–0.236 inch (0.38–6 mm) will typically be suitable.

After extrusion a portion of the tubular segment may optionally be processed to reduce its OD or OD and ID. This may be desired for instance in the case where a reduction of the distal or both the distal and proximal waists of the balloon is desired. For instance, for balloons of about 4.0 mm or larger, the amount of material needed, and the desired stretch ratio for the forming the balloon body can often mandate that the extruded tube have an OD which is larger than the desired final OD of the distal waist. Reducing at least the portion of the tubing segment which will be processed to form the distal portion of the balloon, allows the distal end of the balloon to be made smaller than the OD of the tube as extruded. Although proximal balloon waists are usually larger than distal waists, similar considerations can make it advantageous to likewise reduce a portion of the proximal tube segment which will be formed into the proximal balloon waist. On the other hand for many balloons it is not necessary to reduce any portion of the extruded tubing. ID reduction of the end portions of the tubing segment facilitates preferential expansion of the center, body forming, region of the tubing segment during the pressurized stretching step of the invention.

Reduction of a portion of an extruded tube segment may be accomplished in various ways. A necking reduction may be initiated at a specific location e.g. by kinking or scoring the tube at a specific location. Necking then is accomplished by axially stretching the tubular segment in a manner such that the tube elongates and reduces in both ID and OD from the initiating point. Necking occurs when the material is stretched at a temperature which is about the Tg of the material, or lower. Typical necking temperatures will be in the range of 15–45° C., with ambient room temperature of about 20–25° C. usually being acceptable. Lower necking temperatures are sometimes advantageous.

Another method of reducing a portion of the tube segment is to grind a desired amount of material from the exterior of the tube segment portion. Centerless grinding techniques have been effectively employed to reproducibly remove exterior material from tubes of balloon polymer materials. Grinding may be combined with a subsequent unpressurized or low pressurized stretch which, analogously to the necking step described above will preferentially reduce the ID and further reduce the OD of the ground region without affecting the dimension of the thicker unground region.

A still further method of reducing both ID and OD of a portion of the tube segment is a "cold drawing" step which utilizes differential temperatures applied to different portions of the tube segment during axial stretching. A higher temperature portion of the tube segment will preferentially stretch, reducing its OD relative to the colder portion. For instance, by holding a center portion of the balloon with a cold clamp while pulling on either end of the segment, both proximal and distal end portions of the tubing segment can be reduced while preserving the extruded dimensions of the center segment.

During a stretching reduction step to reduce ID, one end of the tube may be sealed and the interior of the tube pressurized from the other end in order to prevent closure of the interior lumen and to facilitate wall thinning. The pressure in this step should not be so high as to cause the parison to expand radially or burst during the reduction step. Pressure may range from about 0 psi (0 kPa) to about 500 psi (3447 kPa), depending on wall thickness and polymer material.

Figure 2:
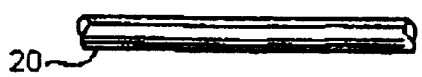
FIG. 2 is a fragmentary side view of an extruded tubular parison suitable for use in preparing a balloon in accordance with the invention.
Figure 3:
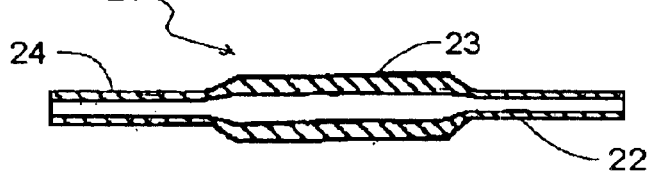
FIG. 3 is a fragmentary schematic sectional view of a parison as in FIG. 2, modified to reduce OD in end portions thereof, prior to the ID expanding axial stretching step of the invention.

FIG. 3 shows a parison 21 which corresponds to parison 20 of FIG. 2 after modification by a reduction step described above. The necked down region of parison 21 is shown at 22. At least a portion 23 of the parison is not necked in this way. Portion 23 when radially expanded will form at least a portion of the body 15 of the finished balloon. For most simple balloons the entire balloon body 15, and at least some of the cone portions 13 and 14 will be formed from unnecked portion 23. In some cases, for instance where the balloon is to be molded into a stepped profile, it may be desirable for only a portion of the balloon body to be formed from portion 23.

After the extruded parison has been formed, the parison is subjected to an ID expanding stretch step in the following manner. One end of the parison is sealed and the parison is pressurized and pulled axially. Temperatures up to the Tg temperature, or even slightly above Tg, may be used. Preferred temperatures range from ambient to just below the Tg. In most cases preferred temperatures will be from about 15° C. to abour 60° C., more preferably from about 20° C. to about 50° C. Pressurization pressure is such that at the selected temperature the ID of the unreduced portion is increased, and the wall thickness is reduced, but the OD is not expanded to the final balloon diameter. Preferably the unnecked ID is expanded by an amount of from about 1.1 to about 2.5, more preferably about 1.4–2.0 times the ID as extruded. Optimal wall thinning amounts will vary depending on the desired final balloon wall thickness. In most cases the pressure selected will be from about 100 psi (689 kPa) to about 800 psi (5515 kPa), although for some combinations of materials and temperatures, pressures as low as 25 psi (172 kPa) or as high as about 1000 psi (6894 kPa), may be suitable. The parison is stretched axially in this step by at least 50% (i.e. to a length of at least 1.5×), preferably from about 2× to about 6×, based on the change in the length of the previously unstretched portion of the parison.

Figure 4:
FIG. 4 is a view as in FIG. 3, after the ID expanding axial stretching step of the invention.
Figure 5:
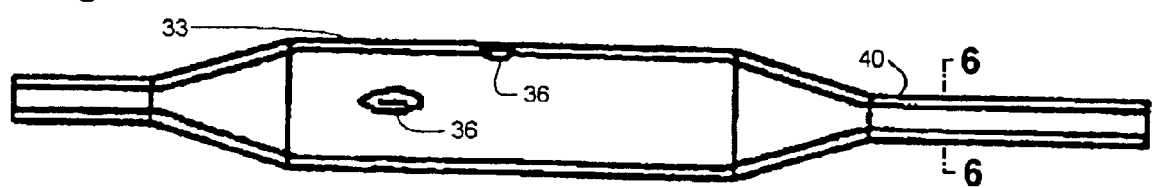
FIG. 5 is a schematic side view of a portion of a balloon produced in the absence of the ID expanding axial stretching step of the invention, and displaying a "football" defect.

FIG. 4 depicts a parison 31, which corresponds to parison 11 in FIG. 2, but after the ID expanding stretching step of the present invention.

In the case where a portion of the parision is reduced in a stretching step, e.g. by necking, grinding/stretching or cold drawing, before the ID expansion step, the reduction and ID expanding stretch steps may be performed in immediate sequence if desired, for instance by increasing the internal parison pressure and/or the parison temperature after the desired region has been reduced. At a pressure and/or temperature higher than used to accomplish the reduction, the larger ID of the region 20 and its lower orientation, will allow it to preferentially expand its ID.

Following the longitudinal stretch step(s), the tubing is blown into an article such as a medical catheter balloon. Free blowing may be used, but typically a mold will be employed. Radial expansion is performed at a temperature above Tg but below melting temperature. For most suitable balloon materials the radial expansion will typically be in the range of about 85–140° C., although in some cases temperatures as high as about 200° C. may be feasible. For medical catheter balloons internal pressure of about 100 (689 kPa) to about 500 psi (3447 kPa) will generally be used to blow the balloon.

If desired, a heat setting step can be run at a temperature higher than the blow temperature (typically 5°–25° C. higher) but at a pressure lower than the blowing pressure (typically 20 psi (138 kPa) to about 100 psi (689 kPa). Heat setting can reduce balloon compliance and can increase the burst pressure of the balloon. Heat setting procedures which may be adapted for use in the inventive process are described in EP 274 411 A2 (C. R. Bard) and EP 592 885 A2 (C. R. Bard), both of which are incorporated herein by reference.

If it is desired to increase compliance or to provide a stepped compliance profile, the blown balloon, or a portion thereof may be shrunk by heating to a temperature somewhat below the blowing temperature (suitably to about 70° C.–80° C.) while pressurizing to at about 30 psi (207 kPa) to about 100 psi (689 kPa). Shrinking procedures which may be adapted for use in the inventive process are described in U.S. Pat. No. 5,348,538 (L. Wang, et al) and in WO 97/32624, both of which are incorporated herein by reference.

The final product is a balloon as in FIG. 1.

Benefits

The inventive process provides several advantages. By allowing post-extrusion modification of the wall thickness and ID before blowing, more flexibility is provided in tailoring balloon properties obtained from a single extrusion run. In this way parisons extruded at a wall thickness previously optimized for a given balloon diameter may also be used to produce comparably optimized balloons of other sizes. This reduces inventory and tooling requirements.

Furthermore, the process of the invention provides a lower level of defects commonly encountered in molded balloons. By expanding the ID prior to blowing, the pressure required to blow the balloon to the mold diameter in the radial expansion step is lessened. A lower blowing pressure produces a slower growth rate in the balloon. This in turn allows for a more uniform distribution of polymer material and produces a lower defect rate. In particular two types of defects are reduced by the inventive process. One is the reduction in the number and size of "fish eye" or "football" defects. Balloon 33 includes a pair of football defects 36 on the body portion thereof. Football defects are believed to be due to regions in which polymer is relatively more gelled than the adjacent polymer material, or to the presence of localized microcontamination causing the defect region to be stressed more. The gelled or microcontaminated material, being less mobile, is not evenly redistributed if the balloon expansion occurs too quickly. With a reduced blowing pressure and consequent balloon growth rate the gelled material has time to redistribute itself more uniformly in the polymer mass.

Figure 6:
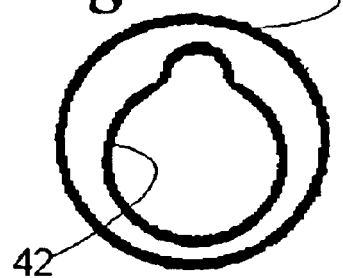
FIG. 6 is a view of the balloon of FIG. 5, taken along line 6—6 of FIG. 5 illustrating a "split waist" defect.

A second type of defect which has been observed to be lessened in balloons produced by the inventive process is the "split waist" defect. As shown in FIG. 6, balloon 33 also displays a split waist defect in the waist 40. In this defect the passageway 42 through the waist is asymmetrically formed.

Because the inventive process reduces the occurrence of such defects, a batch of about 50 or more, and preferably about 100 or more, sequentially produced balloons from a single production run is improved, relatively to a corresponding sequence of balloons produced without the ID expansion step. As such a sequential batch represents a distinctive and non-obvious manufacture, even though the individual non-defective members thereof may not be otherwise readily distinguishable.

The invention is illustrated by the following non-limiting examples

EXAMPLES

Example 1

Catheter balloons of 3.5 and 4.0 mm were formed from extruded tubes of polyamide-polyether-polyester polymer formed in two layers, the inner layer being Pebax® 7233, and the outer layer being Pebax® 4033. The extruded tubes were then subjected to a room temperature stretching step with internal pressurization of the tubing. In control experiments the pressure was set during stretching such that the ID of the tubing remained within ±4% of the ID of the tube as extruded. In the invention examples the pressure was increased such that on stretching the tubing ID grew by 18–30%. The balloons were then blown under identical conditions, except that a pressure was used for the invention examples which was about 50 psi below that which was used to blow the controls. In three lots each of 200 balloons per lot, the scrap rates for football defects for the lots of balloons produced by the invention process was consistently lower (i e. 29%–50% of control scrap rate), than for the controls.

Example 2

A balloon tube 0.0382 inch (0.97 mm) ID×0.0792 (1.98 mm)OD was centerless ground on both ends to an OD of 0.0615 inch (1.56 mm), with a non-ground center region length of 10 mm. The tube was then inserted in a stretching machine which was capable of pressurizing the tube with nitrogen. The tube was stretched at a ratio of 3.7 at ambient temperature, with no pressurization. During this step the end regions stretched essentially exclusively, further reducing their ODs and IDs.

For controls, balloons were produced from these ground and pre-stretched tubes under standard elevated temperature and pressure conditions. The blowing pressure was 470 psi (3241 kPa). A batch of 10 balloons so produced had a football occurrence rate of 30%. The balloons from this batch which did not have this defect had on average a 20 atm burst, double wall thickness of 0.00250 inch (0.064 mm), and a distension of 5.1%

In accordance with the invention, 5 balloons were produced from ground and prestretched tubes as described above which, before blowing had been further modified by pressurizing to 600 psi (4136 kPa) and stretching again. This time the center region stretched essentially exclusively and also began to radially expand. Stretching in this step produced a 60% lengthening of center portion of the tube from its extruded length. The resulting tubes had the following dimensions:

End regions: 0.020×0.036 inch (0.51×0.91 mm)

Center region: 0.0799×0.0876 inch (2.03×2.23 mm)

This further processing allowed the balloons to be blown at a pressure of 250 psi (1724 kPa). Otherwise the processing for these balloons was the same as the controls. None of the balloons displayed football defects. The balloons had a burst pressure of 20 atmospheres and a double wall thickness of 0.00240 inch (0.061 mm).

While the invention has been described in connection with what is presently considered to be the most practical and preferred embodiments, it is to be understood that the invention is not to be limited to the disclosed embodiments but, on the contrary, is intended to cover various modifications and equivalent arrangements included within the spirit and scope of the appended claims.

The above examples and disclosure are intended to be illustrative and not exhaustive. These examples and description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto. Further, the particular features presented in the dependent claims below can be combined with each other in other manners within the scope of the invention such that the invention should be recognized as also specifically directed to other embodiments having any other possible combination of the features of the dependent claims.

The entire contents of all documents and copending applications mentioned anywhere in the present application are incorporated herein by reference.

What is claimed is:

1. A process for producing a balloon comprising:
    (a) axially stretching an extruded tubing segment made of a polymer material while pressurizing the tubing at an internal pressure above ambient pressure, to produce a stretched parison, the tubing segment having a first internal diameter and the polymer material having a glass transition temperature above ambient temperature, and then
    (b) blowing the balloon by expanding the stretched parison in a mold at a temperature above said glass transition temperature,
wherein said axially stretching comprises a step (a)(i) of subjecting the tubing to a temperature and internal pressure which is sufficient to expand the internal diameter of at least a portion A of the stretched parison to a second internal diameter greater than the first internal diameter while axially pulling the tubing.

2. A process as in claim 1 wherein the polymer material includes a polymer selected from the group consisting of olefin/ionomer copolymers; polyesters; polyamides; polyurethanes; polyetheretherketone; polycarbonates; poly(meth)acrylates; maleate polymers; and block copolymers having polyester or polyamide segments.

3. A process as in claim 1 wherein the polymer material includes a polymer selected from the group consisting of polyamide/polyether/polyester, polyamide/polyether, and polyester/polyether block copolymers; ethylene terephthalate polymers and copolymers; butylene terephthalate polymers and copolymers; ethylene naphthalate polymers and copolymers; and polyamides.

4. A process as in claim 1 wherein said extruded tubing segment is formed of a single layer of polymer material.

5. A process as in claim 1 wherein said extruded tubing segment is formed of at least two layers of polymer material.

6. A process as in claim 1 wherein the balloon comprises a body portion having proximal and distal ends; proximal and distal cone portions, the cone portions being respectively located adjacent the respective proximal and distal ends of the balloon body; and proximal and distal waist portions adjacent the respective proximal and distal cone portions, and wherein, in step (b), said portion A of the stretched parison forms at least the balloon body.

7. A process as in claim 6 wherein the stretched parison comprises a second portion B1 having an ID which is not greater than the first internal diameter and in step (b) one of the waist portions of the balloon is formed from said portion B1.

8. A process as in claim 7 wherein said axial stretching further comprises a the step (a)(ii), of forming said stretched parison portion B1 by reducing a portion of the extruded tubing segment to an internal diameter less than said first internal diameter prior to said step (a)(i).

9. A process as in claim 7 wherein portion B1 of the stretched parison forms the distal waist portion of the balloon, and the stretched parison comprises a third portion (B2) having an ID which is not greater than the first internal diameter, and in step (b) the proximal waist portion of the balloon is formed from said portion B1.

10. A process as in claim 9 wherein said axial stretching further comprises the a step (a)(ii), of forming at least one of said stretched parison portion B1 and B2 by necking down a portion of the extruded tubing segment to an ID less than said first internal diameter.

11. A process as in claim 7 wherein said step (a)(ii) is performed at a pressure or temperature which is less than the respective pressure or temperature employed in step (a)(i).

12. A process as in claim 1 wherein in step (a)(i) the pressure is in the range of 25–1000 psi (172–6894 kPa) and the temperature is in the range of 15–60° C.

* * * * *